United States Patent
Arndt et al.

(10) Patent No.: US 7,197,933 B2
(45) Date of Patent: Apr. 3, 2007

(54) ULTRASONIC SENSOR FOR CONTROLLING THE PROCESS DURING RESISTANCE SPOT WELDING

(75) Inventors: Volker Arndt, Erbach (DE); Michael Lach, Erkrath (DE); Michael Platte, Wuppertal (DE); Heinz-Ullrich Mueller, Michelstadt (DE)

(73) Assignees: Robert Bosch GmbH, Stuttgart (DE); Karl Deutsch Pruef- und Messgeraetebau GmbH & Co. KG, Wuppertal (DE)

( * ) Notice: Subject to any disclaimer, the term of this patent is extended or adjusted under 35 U.S.C. 154(b) by 29 days.

(21) Appl. No.: 10/470,978

(22) PCT Filed: Feb. 4, 2002

(86) PCT No.: PCT/DE02/00392

§ 371 (c)(1),
(2), (4) Date: Dec. 10, 2003

(87) PCT Pub. No.: WO02/061413

PCT Pub. Date: Aug. 8, 2002

(65) Prior Publication Data

US 2004/0079156 A1    Apr. 29, 2004

(30) Foreign Application Priority Data

Feb. 2, 2001  (DE) ............................. 101 04 608

(51) Int. Cl.
*G01N 29/24*  (2006.01)

(52) U.S. Cl. ..................... 73/644; 73/632; 73/629; 219/109

(58) Field of Classification Search .......... 73/597–600, 73/644, 599, 629, 632; 219/117.1, 109, 110
See application file for complete search history.

(56) References Cited

U.S. PATENT DOCUMENTS

| | | | | |
|---|---|---|---|---|
| 2,432,750 A | * | 12/1947 | Goldsworthy | 219/78.14 |
| 3,789,183 A | * | 1/1974 | Conley | 219/92 |
| 4,341,940 A | * | 7/1982 | Defourny | 219/117.1 |
| 4,734,555 A | * | 3/1988 | Ferguson | 219/109 |
| 4,918,990 A | | 4/1990 | Fowler | |

(Continued)

FOREIGN PATENT DOCUMENTS

DE    199 37 479 A    3/2001

(Continued)

OTHER PUBLICATIONS

Waschkies E: "Pruefen des Widerst Ands-Punktschweissprozesses mit . . . " Schweissen und Schneiden, Deitscher Verlag Fuer Schweisstechnik. Duesseldorf, DE Bd. 49, Nr. 1, 1997, Seiten 15-19.

*Primary Examiner*—Hezron Williams
*Assistant Examiner*—Nashmiya Fayyaz
(74) *Attorney, Agent, or Firm*—Michael J. Striker

(57) ABSTRACT

A sensor carrier is provided that has at least one oscillating element (32) that introduces ultrasonic waves into an area to be examined and/or receives ultrasonic waves coming from the area to be examined, whereby the oscillating element (32) is located in an oscillator carrier (33), and the oscillator carrier (33) has connecting means (36, 37, 38, 39) for connection with the electrode (31).

13 Claims, 2 Drawing Sheets

U.S. PATENT DOCUMENTS

| | | | | |
|---|---|---|---|---|
| 4,976,150 | A * | 12/1990 | Deka | 73/644 |
| 5,920,014 | A * | 7/1999 | Waschkies | 73/597 |
| 6,414,260 | B1 * | 7/2002 | Vogt | 219/109 |
| 2004/0206728 | A1 * | 10/2004 | Platte et al. | 219/109 |
| 2005/0077268 | A1 * | 4/2005 | Vogt et al. | 219/55 |

FOREIGN PATENT DOCUMENTS

| | | | |
|---|---|---|---|
| EP | 0 653 061 A | | 5/1995 |
| JP | 60231575 A | * | 11/1985 |
| JP | 215384 | * | 9/1988 |
| JP | 29432 A | * | 2/1997 |
| RU | 1206034 A | * | 1/1986 |
| WO | 99 51384 A | | 10/1999 |

* cited by examiner

ULTRASONIC SENSOR FOR CONTROLLING THE PROCESS DURING RESISTANCE SPOT WELDING

BACKGROUND OF THE INVENTION

The present invention relates to an ultrasonic sensor for controlling the process during resistance spot welding.

The essence of the method described in European Patent Application EP-A-653 061 is to investigate the intended weld region by ultrasonic transmission during the welding operation using shear and transversal waves by positioning an ultrasonic transmitter and an ultrasonic receiver for shear waves on each of the external electrode adapters of the two diametrically opposed welding electrodes. Starting at the ultrasonic transmitter on one welding electrode, the ultrasonic signal passes through the weld material—two or more sheets to be welded—and the other welding electrode until it reaches the ultrasonic receiver. Said ultrasonic receiver converts said ultrasonic signal to a measurable electrical signal U, the shape of the curve of which over time can be depicted using the equation $U=U_O \cdot \sin\omega t$, where $\omega=2\pi f$ is the angular frequency of the ultrasonic wave, f is the frequency, and t is the time. The through-transmitted signal is detected online, and its amplitude $U_O$ is used as the control variable for amplitude and the shape of the welding current curve over time. The transversal wave is selected because the influence of fluid formation in the weld nugget on the dampening of a through-transmitted wave is very strong with this type of wave. The amplitude $U_O$ of the transversal wave, which changes markedly and in characteristic fashion over the course of the welding process, permits a reliable determination of the formation and size of the weld nugget and can therefore be used as a manipulated variable for a control process.

The basic feasibility of the method and the reliability of the examination findings are crucially dependent on the ultrasonic sensors used, their location relative to the welding electrodes, and the sound propagation inside the welding electrodes. In the realization according to EP-A-653 061, an arrangement of ultrasonic sensors is selected in which the ultrasonic transmitter and ultrasonic receiver are mounted on the external electrode adapters or on the electrode holders, which are not shown in the drawing. Shear waves, transversal waves, or torsional waves having a frequency of less than 1 MHz are generated. It is stated that it is particularly advantageous to generate horizontally polarized transversal waves, since they have a low tendency to undergo undesired mode changes when reflections occur inside the sound-directing electroder holder. The ultrasonic transmitters and receivers are "shear wave test heads". They contain flat and, usually, round piezoelectric plates having a diameter ranging from a few mm to a few cm, and that execute a shearing motion when excited with electric voltage or, conversely, when they receive, they react to a received shear wave with a reception voltage. Since, when a shear wave test head of this type is mounted directly on the external electrode adapter, the main emission direction of the sound would not be directed in the direction of the weld material, but rather at the center of the electrode, wedge-shaped attachments are preferably used, that are installed between the test heads and the welding electrodes and permit the main emission direction of the test head to be aligned with the weld material at an angle that is markedly less than 90°, e.g., approximately 45°. This arrangement does now allow all of the sound energy that is produced to be concentrated in the direction of the welding spot, however.

German Patent Application DE-A-199 37 479, which was published at a later date, describes an ultrasonic sensor system that is improved in this regard. With said ultrasonic sensor system, the piezoelectric shear wave plate or a complete shear wave test head is installed in a recess inside the electrode adapter for transmitting and/or receiving. In fact, said piezoelectric shear wave plate or the complete shear wave test head is installed in such a manner that the piezoelectric plate is oriented almost perpendicular to the electrode adapter, and the main emission direction of the transmitter and the main reception direction of the receiver are therefore parallel to the electrode adapter and are directed toward with each other. This allows all of the ultrasonic energy that is produced to be concentrated in the direction of the welding spot and, from there, it is transmitted in the direction of the receiver. This allows such a level of ultrasonic intensity to be produced in the welding spot and, during reception, it allows a received signal to be generated that is so great that a much greater wanted-to-unwanted signal ratio exists with regard for the further evaluation for controlling the welding process.

In the case of the latter sensor system, described in German Patent Application DE-A-199 37 479, in which the sensors are integrated in specially-configured welding electrodes and that is optimized with regard for the wanted-to-unwanted signal ratio of the ultrasonic signals, it is also considered disadvantageous that the electrode adapters typically used with spot welding can no longer be used. It was possible to manufacture said electrode adapters as a simple turned component at very low cost, due to their smooth cylindrical shape. With the sensor system according to German Patent Application DE-A-199 37 479, however, the complete welding electrode with integrated sensor must be replaced if mechanical damage occurs to the electrode adapter or if a sensor defect occurs.

With resistance spot welding, however, a large number of weld objects have different shapes, so a large number of welding electrodes having different shapes is used. Since the diameter of the welding electrodes is the same for most applications, the large variety of different types is due mainly to the welding electrodes having different lengths and the end pieces having different shapes, which said end pieces must be accommodated by corresponding electrode holders. There are also many different types of said electrode holders. For this reason, one must put up with a large variety of different types of welding electrodes having integrated sensors with regard for the acoustically optimized sensor system according to German Patent Application DE-A-199 37 479 as well.

With regard for the sensors mounted on the external electrode adapter, no statements are made in European Patent Application EP-A-653 061 about how the shear wave test heads, including the wedge-shaped attachments, are mounted on the external electrode adapter. This is a fundamental problem. Not only must the connection have good acoustic conductivity, it must also be so mechanically sound that the sensors and/or wedge-shaped attachments are able to withstand the high accelerations that occur when the welding tongs open and close during the welding process and not drop out of the welding electrodes when the welding electrodes impact the sheets to be welded. Since, in addition, considerable temperature fluctuations can occur at the welding electrodes, an adhesive connection is not suitable. This would also prevent easy replacement of the sensors.

The object of the present invention, therefore, is to provide an ultrasonic sensor for controlling the process during resistance spot welding, in which the sensors and test heads are oriented entirely in the direction of the welding spot and are mounted on the external adapter of preferably cylindrically shaped welding electrodes in such a manner that simple installation and replacement is enabled.

SUMMARY OF THE INVENTION

The sensor carrier according to the invention has at least one oscillator element that introduces ultrasonic waves into an area to be examined and/or receives the ultrasonic waves coming from the area to be examined, whereby the oscillator element is located in an oscillator carrier, and the oscillator carrier includes connecting means for connection with an electrode or electrode adapter of a welding system. The connecting means ensure, in simple fashion, that the complete sensor system need not be replaced when the welding electrode becomes worn. The connecting means are therefore designed to be detachable, so that, when the welding electrodes are replaced, the oscillator carrier is first removed from the electrode or the electrode adapter and then reinstalled in the new electrode. The sensor carrier according to the invention further makes it possible to use conventional, commercially available electrodes for the resistance welding system to be used, which said electrodes are subsequently equipped with the sensor carrier.

In an advantageous further development, the sensor carrier is capable of being joined with the electrode in a positively-interlocking manner. As a result, the ultrasonic waves—which are preferably configured as shear waves—propagate easily from the oscillator carrier through the electrode to the area to be investigated by ultrasonic transmission. An advantageous embodiment further provides that the oscillator carrier is designed annular in shape, with an inner diameter that corresponds to the outer diameter of the welding electrode with an exact fit. In addition, the oscillator carrier has a slotted design, whereby the connecting means are designed as a clamping device that, in the clamped state, establish a bonded connection between the outer surface of the welding electrode and the inner surface of the oscillator carrier in order to transfer ultrasonic waves. The oscillator element is so positioned that its face normal is oriented nearly parallel to the central axis of the annular oscillator carrier, or it forms an angle with said central axis that does not exceed 15 degrees. This ensures that the ultrasonic waves are certain to reach the area to be investigated. The advantage of the proposed arrangement is its simple handling in terms of replacing the sensor carrier. Said proposed arrangement also ensures that the ultrasonic waves are certain to reach the electrode and the area to be investigated. With the clamping device that has a gap, it is also ensured that the sensor carrier is capable of being mounted on electrodes having a slightly deviating diameter without having to provide different sensor carriers in each case for different electrodes.

In an advantageous further development, it is provided that the acoustic impedance of the material of the oscillator carrier is similar to that of the material of the welding electrode. As a result, the ultrasonic transmission from the oscillator carrier to the welding electrode can be further improved.

Further advantageous developments result from the further dependent claims and the description.

BRIEF DESCRIPTION OF THE DRAWING

An exemplary embodiment is shown in the drawing and is described in greater detail hereinbelow.

Using a simple exemplary embodiment of a sensor for controlling the process during resistance spot welding, FIG. 1 shows the basic design and mode of operation of the present invention. FIG. 1b is a top view of the sensor arrangement according to FIG. 1a.

FIG. 2 shows the sketched wave fronts of the sound emission added to FIG. 1a.

DETAILED DESCRIPTION OF THE PREFERRED EMBODIMENTS

Figure 1A:
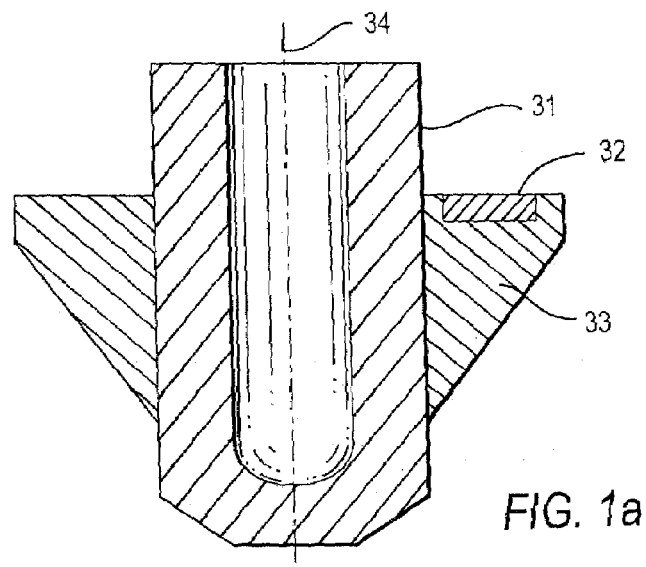
FIG. 1a is a sectional drawing through the welding electrode with the sensor mounted thereon.

In particular, the invention utilizes the physical effect that a low-frequency (<1 MHz) shear wave—as proposed according to European Patent Application EP-A653 061 for controlling the process during resistance spot welding, or, in general, any other waveform of a correspondingly low-frequency ultrasonic wave that is introduced into a welding electrode that is cylindrical and hollow inside in order to accommodate cooling water—propagates more or less homogeneously through the entire cross section of the welding electrode on its way to the receiver on the other welding electrode. This is due to the fact that, below a frequency of 1 MHz, at typical propagation speeds of 3000 m/s, the wavelength of the shear wave in the cylindrical shaft of the welding electrode ranges from a few millimeters to a few centimeters. Welding electrodes typically have an outer diameter of 15–30 mm, and their walls are typically 4–8 mm thick. The cross section of the electrode adapter is therefore of an equal or smaller order of magnitude than the wavelength. The cross section of the welding electrode itself is already such a small aperture opening for the propagating ultrasonic wave that a largely undirectional propagation of sound takes place, and the sound wave fills the entire cross section of the electrode adapter after just a short path of travel.

An annular oscillator carrier 33 is located around the cylindrical shaft of the welding electrode 31. The inner diameter of the annular oscillator carrier 33 is so selected that it is oversized only slightly compared to the outer diameter of the welding electrode 31, enabling the oscillator carrier 33 to be slid, with an exact fit, onto the shaft of the welding electrode 31 and to be removed just as easily. The oscillator carrier 33 is slotted on one side. A narrow gap 38 is located at the slotted point. Material recesses 35.1 and 35.2, a through hole 36 and a threaded hole 37 are formed in the oscillator carrier 33 to the left and right of the gap 38, enabling the two legs of the oscillator carrier 33 to be pulled together when the screw 39 is screwed into the threaded hole 37, and the width of the gap 38 is reduced. Once the oscillator carrier 33 is slid onto the welding electrode 31, the screw 39 located in the thread 37 is tightened to clamp the oscillator carrier 33 tightly and flush with the welding electrode 31. Depending on the draw-in force of the screw 39, the inner surface of the oscillator carrier 33 and the outer surface of the welding electrode 31 then form a more or less bonded connection with each other, across which a low-frequency ultrasonic wave can be easily transmitted, even without installing coupling means.

Figure 1B:
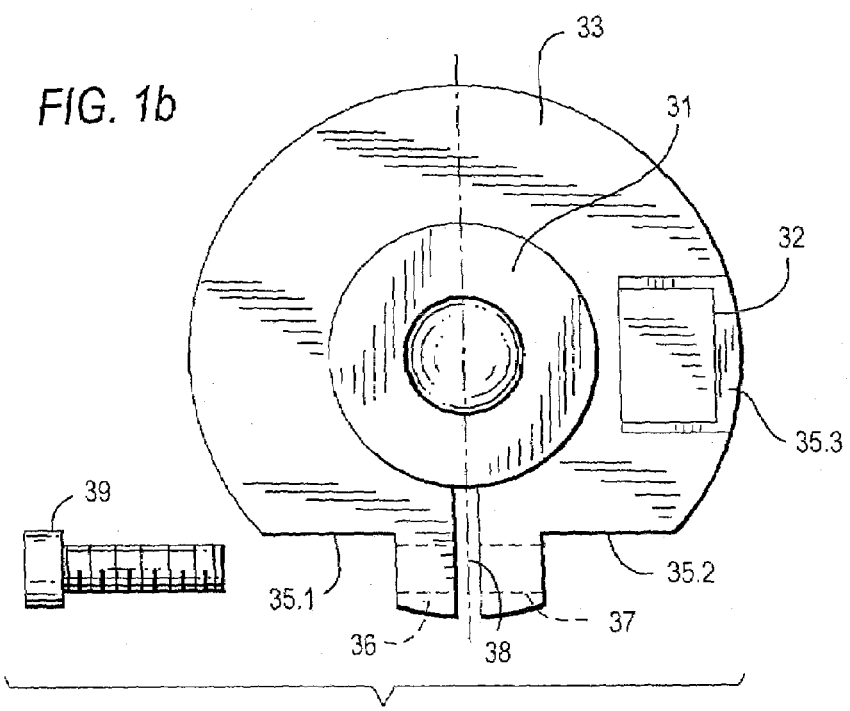

A further material recess 35.3 is located in the oscillator carrier 33, in which a piezoelectric oscillator element 32 or a complete ultrasound test head is inserted. In FIG. 1, rectangular piezoelectric oscillator elements are used. Basically speaking, however, said oscillator elements can have another geometric form (e.g., round, semicircular, or rhombic) as well.

Figure 2:
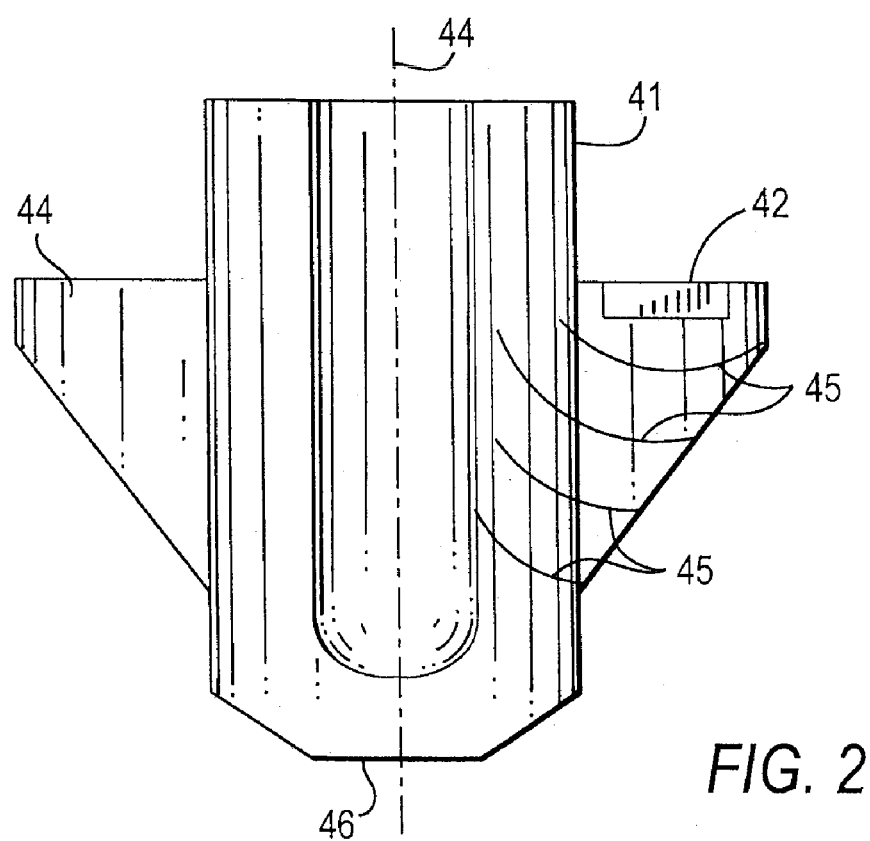

Oscillator element 32 is so positioned in oscillator carrier 33 that the face normal of oscillator carrier 33—which is identical to the main emission direction—extends parallel to central axis 34, so that, during transmission, the sound is emitted in the direction of the welding spot. At low frequencies (<1 MHz) and with oscillator dimensions that are not too great (e.g., <20 mm), the wavelength of the ultrasound that is produced is of the same order of magnitude as the edge length of the oscillator element 32, or it is even greater than the latter. This is why the sound emission is virtually undirectional and spherical, as indicated in the sketched wave fronts 45 in FIG. 2. The entire ultrasonic wave generated by the piezoelectric oscillator element 32 therefore travels from the electrode adapter 31 to the oscillator carrier 33 after just a short path of travel.

During reception, the same considerations basically apply for a low-frequency ultrasonic wave emitted from the base 46 with regard for the spacial propagation of sound in the welding electrode 31 and the oscillator carrier 33. For this reason, the sensor system described can be used as a transmitter and a receiver: due to the large wavelength of the sound wave and the small dimensions of the welding spot and/or the base 46 of the welding electrode 31, this cross section—as well as any other cross section—of the welding electrode 31 forms a small aperture opening, so that an almost spherical propagation of sound would take place without any lateral material restrictions. During reception, therefore, a greater portion of the sound energy also reaches the oscillator element 32. Since its surface is also oriented almost parallel to the wave front, a very high reception voltage can be picked off between the top side and bottom side of the piezoelectric element.

In order to optimize the alignment of the oscillator element 32 with the wave front, said oscillator element 32 can be tilted slightly, so that the face normals of the oscillator element 32 and the axis 41 form an angle having few angular degrees. In order to optimize the waveform of oscillation, the piezoelectric oscillator elements 32 can be equipped with a damping element on the back side.

In addition, acoustic adaptive layers can be located between the oscillator carrier and the piezoelectric oscillating elements.

In order to prevent acoustic reflections between oscillator carrier 33 and welding electrode 31 during sound transmission, a material can be selected that has an acoustic impedance (the product of density and sound propagation velocity) that corresponds to that of the material used to make the welding electrodes 31.

Refractive effects are prevented by selecting a material for the oscillator carrier 33 having a sound propagation velocity that corresponds to that of the material used to make the welding electrodes 31.

Piezoelectric transducers can also be designed and manufactured having a stacked configuration. This technique can be used advantageously with regard for the present invention. When n elements are electrically connected in parallel, it is possible to generate acoustic amplitudes that are n-fold higher during transmission, for instance, and to generate quantities of charge that are n-fold greater during reception, with excitation voltage remaining the same.

What is claimed is:

1. A sensor carrier for an elongated welding electrode (31) having at least one oscillating element (32) that introduces ultrasonic waves into an area to be examined, or both introduces ultrasonic waves into the area to be examined and receives ultrasonic waves coming from the area to be examined via the welding electrode, whereby the oscillating element (32) is located at or in a hollow oscillator carrier (33) outside of the welding electrode (31), wherein the oscillator carrier (33) has connecting means (36, 37, 38, 39) for connection with the welding electrode (31), wherein the oscillator carrier (33) is configured as a carrier which is elongated in a longitudinal direction corresponding to an elongation of the welding electrode (31), and is annular and has a cylindrical portion which carries the oscillating element (32) and a conical portion which extends from the cylinder portion and has an outer diameter reducing in the longitudinal direction, such that an inner diameter of the oscillator carrier approximately corresponds to an outer diameter of the welding electrode (31) thereby enabling the oscillator carrier (33) to be slid, onto the shaft of the welding electrode (31) and to be removed readily from the shaft of the welding electrode and wherein the cylindrical portion of the oscillator carrier (33) has an axial top end face facing away from the conical portion, and wherein the oscillating element (32) is arranged on the axial top end face of the cylindrical portion of the oscillator carrier(33).

2. The sensor carrier as recited in claim 1, wherein the connecting means (36, 37, 38, 39) establish a detachable connection between the oscillator carrier (33) and the welding electrode (31).

3. The sensor carrier as recited in claim 1, wherein the oscillator carrier (33) is designed positively-interlockirig with the electrode (31).

4. The sensor carrier as recited in claim 1, wherein the at least one oscillating element (32) has a stacked configuration and is composed of at least two piezoelectric plates or disks that are stacked one on top of the other, in alignment with each other.

5. The sensor carrier as recited in claim 1, wherein the connecting means (36, 37, 38, 39) are designed as a clamping device provided on one radial side of the oscillator carrier.

6. The sensor carrier as recited in claim 1, wherein the oscillator carrier (33) has a slit (38) provided on only one radial side of the oscillator carrier (33l and extending in a longitudinal direction of the oscillator carrier, said slit being adjustable by the connecting means (36, 37, 38, 39) provided on said only one radial side of the oscillator carrier (33) in order to produce a positively-interlocking connection with the electrode (31).

7. The sensor carrier as recited in claim 1, wherein the at least one oscillating element (32) is so positioned that a normal to a face of the at least one oscillating element is oriented almost parallel to a central axis of the oscillator carrier (33), or it the face forms an angle with said central axis that does not exceed 15 degrees.

8. The sensor carrier as recited in claim 1, wherein the at least one oscillating element (32) is a shear wave plate.

9. The sensor carrier as mailed in claim 1, wherein the at least one oscillating element (32) has a damping element on a back side.

10. The sensor carrier as recited in claim 1, wherein acoustic adaptive layers are located between the at least one oscillating element (32) and the oscillator carrier (33).

11. The sensor carrier as recited in claim 1, wherein the acoustic impedance of the material of the oscillator carder (33) is similar to that of the material of the welding electrode (31).

12. The sensor carder as recited in claim 1, wherein the sound propagation velocity of the material of the oscillator carrier (33) is similar to that of the material of the welding electrode (31).

13. The sensor carrier as recited in claim 1, wherein the frequency of the at least one oscillating element (32) is less than 1 MHz.

* * * * *